United States Patent
Li et al.

(10) Patent No.: US 11,732,276 B2
(45) Date of Patent: *Aug. 22, 2023

(54) USE OF GENOMIC NW_006882077.1 IN CHO CELL FOR STABLY EXPRESSING A PROTEIN

(71) Applicant: Jiangnan University, Wuxi (CN)

(72) Inventors: Huazhong Li, Wuxi (CN); Yun Chen, Wuxi (CN); Jian Jin, Wuxi (CN); Songtao Zhou, Wuxi (CN); Zuoying Duan, Wuxi (CN); Xiaohai Gong, Wuxi (CN)

(73) Assignee: Jiangnan University, Wuxi (CN)

( * ) Notice: Subject to any disclaimer, the term of this patent is extended or adjusted under 35 U.S.C. 154(b) by 583 days.

This patent is subject to a terminal disclaimer.

(21) Appl. No.: 16/644,955

(22) PCT Filed: Dec. 3, 2018

(86) PCT No.: PCT/CN2018/118888
§ 371 (c)(1),
(2) Date: Mar. 5, 2020

(87) PCT Pub. No.: WO2020/087641
PCT Pub. Date: May 7, 2020

(65) Prior Publication Data
US 2021/0238634 A1    Aug. 5, 2021

(30) Foreign Application Priority Data

Oct. 30, 2018   (CN) .......................... 201811274640.6

(51) Int. Cl.
*C12N 15/90*    (2006.01)
*C12N 5/071*    (2010.01)
*C12N 15/85*    (2006.01)

(52) U.S. Cl.
CPC ......... *C12N 15/907* (2013.01); *C12N 5/0682* (2013.01); *C12N 15/85* (2013.01); *C12N 2510/02* (2013.01); *C12N 2810/10* (2013.01)

(58) Field of Classification Search
CPC .... C12N 15/907; C12N 5/0682; C12N 15/85; C12N 2510/02; C12N 2810/10
See application file for complete search history.

(56) References Cited

FOREIGN PATENT DOCUMENTS

| CN | 107557390 A | 1/2018 |
| CN | 107723276 A | 2/2018 |
| WO | 2018148196 A1 | 8/2018 |

OTHER PUBLICATIONS

Zhou, S et al. CN107557390A machine translation, p. 1-16. 2018. (Year: 2018).*
David L Hacker et al., Recombinant protein production from stable mammalian cell lines and pools, Current Opinion in Structural Biology, 2016, pp. 129-136, 38.
Hong Zhou et al., Strategies to Improve the Stability of Protein Production from High Level Expression Recombinant CHO Cells, Letters in Biotechnology, 2006, pp. 945-949, vol. 17 No. 6.
Jiaxian Wang et al., Application of Crispr/Cas9 Technology in Targeted Gene Integration in CHO cells, Chinese Journal of Pharmaceuticals 2017, pp. 33-36, 48(1).
Jae Seong Lee et al., Site-specific integration in CHO cells mediated by CRISPR/Cas9 and homology-directed DNA repair pathway, Scientific Reports, 2015, pp. 1-11, 5 : 8572.
Jae Seong Lee et al., Accelerated Homology-Directed Targeted Integration of Transgenes in Chinese Hamster Ovary Cells Via CRISPR/Cas9 and Fluorescent Enrichment, Biotechnology and Bioengineering, 2016, pp. 2518-2523, 10.113, vol. 11.
Menglin Zhao et al., Rapid development of stable transgene CHO cell lines by CRISPR/Cas9-mediated site-specific integration into C12orf35, Applied Microbiology and Biotechnology, 2018 pp. 6105-6117, 102.

* cited by examiner

*Primary Examiner* — Paul J Holland
(74) *Attorney, Agent, or Firm* — Bayramoglu Law Offices LLC

(57) ABSTRACT

Use of genomic NW_006882077.1 in CHO cell for stably expressing a protein is disclosed. The certain site in CHO cell genome for stably expressing a protein is positioned at a base of No. 691045 in a CHO cell gene NW_006882077.1; a sequence of 5' NNNNNNNNNNNNNNNNNNNNNGG3' that can be identified by CRISPR/Cas9 technology and positioned in a base range of No. 690980-691090 around the certain site is a target sequence. Various of protein genes are introduced into a fixed site in CHO cell genome, and expressed stably in the present disclosure.

9 Claims, 1 Drawing Sheet
Specification includes a Sequence Listing.

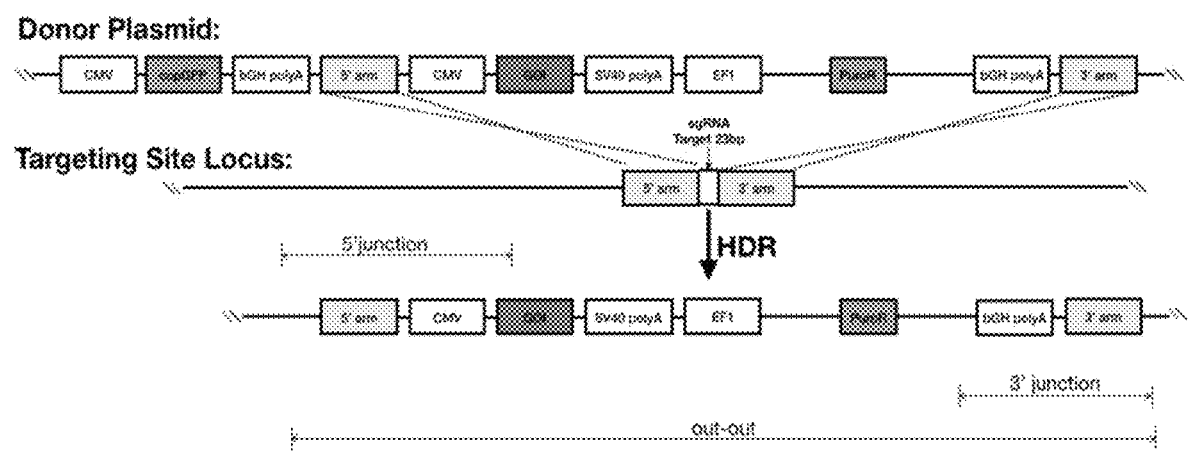

USE OF GENOMIC NW_006882077.1 IN CHO CELL FOR STABLY EXPRESSING A PROTEIN

CROSS REFERENCE TO THE RELATED APPLICATIONS

This application is the national phase entry of International Application No. PCT/CN2018/118888, filed on Dec. 3, 2018, which is based upon and claims priority to Chinese Patent Application No. 2018112746406, filed on Oct. 30, 2018, the entire contents of which are incorporated herein by reference.

REFERENCE TO SEQUENCE LISTING

The instant application contains a Sequence Listing which has been submitted in ASCII format via EFS-Web and is hereby incorporated by reference in its entirety. The ASCII copy is named "GBHY034_ST25-20230303.txt", created on Mar. 3, 2023, and is 2,495,459 bytes in size.

TECHNICAL FIELD

The present disclosure relates to the field of genetic technology, particularly to gene recombination in a CHO cell for stably expressing a protein.

BACKGROUND

Chinese Hamster Ovary (CHO) cell is an important cell line used in biopharmaceuticals. Many different types of CHO cell lines have been developed including a cell line that can be used to expand gene copy numbers. However, by increasing transgene copy number is not correlated well with the increase in express level of the target protein. Also the expression level of most CHO cells is unstable even with increased protein expression. The current mostly used method of constructing stable transfected cells is time-consuming and labor-intensive, mainly due to repetitive monoclonal screening processes. Thus, it is currently expected in the field of cell line construction that a method of obtaining a cell expressed stably and in a high level within a short time, and can ensure that the constructed recombinant cell line has the same quality level as traditional methods to ensure regulatory approval.

A traditional method of constructing an exogenous protein-expressing cell line is to randomly integrate an exogenous gene into the cell genome, which is subjected to screening of a series of high-expressing monoclonal cells, to obtain a cell line with a high expressing of exogenous protein. Due to the diversity of site effect differences, the recombinant cells produced by random integration have different expression levels. It takes a long time and many steps to select high-expressing monoclonal cells. Monoclonal cells obtained through random integration cannot guarantee stably expressing peptides/proteins in cell passages, and monoclonal screening needs to be repeated at each time a recombinant cell is constructed, increasing the cost of research and development of biopharmaceuticals.

The site effect hinders the efficiency of traditional random integration to construct recombinant cell lines. Repetitive high-expression monoclonal screening is time-consuming, labor-intensive and expensive. How to overcome the site effect and to obtain quickly and efficiently stable expressing monoclonal cells by using the site-specific integration technology has been discussed in the art for many years, and there has been no breakthrough progress.

SUMMARY

In view of the above problems in the prior art, the applicant of the present disclosure provides use of NCBI GenBank accession number genomic NW_006882077.1 (SEQ ID NO: 11) in CHO cell for stably expressing a protein. In the present disclosure, different protein genes are introduced into the CHO cell genome at a fixed position and expressed stably. In addition, in the process of achieving the site-specific integration, there is no need to select repeatedly monoclonal cells to obtain cell lines with higher expression, which saves a lot of time.

The technical solution of the present disclosure is as follows.

Use of a certain site in CHO cell genome for stably expressing a protein, wherein the site in CHO genome for stably expressing a protein is positioned at a base of No. 691045 in a CHO cell gene NW_006882077.1;

a sequence of 5' NNNNNNNNNNNNNNNNNNNNNGG3', as shown in SEQ ID NO:10, that can be identified by CRISPR/Cas9 technology and positioned in a base range of No. 690980-691090 around the certain site is a target sequence.

The protein is one having a molecular weight of less than 160 KDa.

The protein is one selected from the group consisting of red fluorescence protein, polypeptide, a functional protein, an antibody, and a fusion protein.

The target sequence is the bases positioned at No. 691068-691090, around the base of No. 691045 in the CHO cell gene NW_006882077.1.

Further, the target sequence is 5'-GATCTAACTTGGCTTGCCTGAGG-3', as shown in SEQ ID NO:1.

The target sequence is 5'-TGCAACTCTCAGATCTAACTTGG-3', as shown in SEQ ID NO:2.

The target sequence is 5'-GAGAGTTGCAGTAACGAAAGTGG-3', as shown in SEQ ID NO:3.

The target sequence is 5'-GAGTTAACTAAAGTGACTGAAGG-3', as shown in SEQ ID NO:4.

The target sequence is 5'-TCAAGAACAGATGCTGAAGAAGG-3', as shown in SEQ ID NO:5.

The target sequence is 5'-GCTGAAGAAGGTAATAGCATTGG-3', as shown in SEQ ID NO:6.

The present disclosure provides a recombinant donor carrier containing the target sequence for expressing the protein.

The recombinant donor carrier is a carrier for CHO cell expression.

The recombinant donor carrier is prepared by inserting a protein gene into a region between the 5'arm and 3'arm of the plasmid, so that the nucleotide sequence is located downstream of the promoter and is regulated by the promoter to obtain a recombinant CHO cell expression plasmid.

The promoter is one selected from the group consisting of CMV (a strong promoter for expression in a mammalian cell derived from human cytomegalovirus), EF-1a (a strong promoter for expression in a mammalian cell derived from human elongation factor 1α), SV40 (a promoter for expression in a mammalian cell derived from simian vacuole virus 40), PGK1 (a promoter for expression in a mammalian cell derived from phosphoglycerate kinase gene), UBC (a promoter for expression in a mammalian cell derived from human ubiquitin C gene), human beta actin (a promoter for expression in a mammalian cell derived from β-actin gene), and CAG (a strong hybrid promoter for expression in a mammalian cell).

Also provided is a recombinant CHO cell line for expressing a protein.

Further provided is a method for expressing a protein by a gene in a CHO cell including (1) transforming a CHO cell with a recombinant donor carrier to obtain a recombinant CHO cell;

(2) culturing the recombinant CHO cell on a plate, and collecting the supernatant to detect the expression level, and adapting an adherent recombinant CHO cell to suspension culture;

(3) culturing the adopted recombinant CHO cell in a shake flask and determining the protein expressing level.

The present disclosure also provides a selection of a stable expression site in a CHO cell genome:

1) constructing a lentivirus with a fluorescent label and calculating its titer; integrating igk-luc gene to a multiple cloning site on pLVX-CMV-MCS-T2A-Zsgreen carrier, followed by performing three plasmid transfection to HEK-293T cell by using plasmids of pSPAX2 and pMD2G, aspirating the supernatant twice at 48 h and 72 h, collecting and then ultra-centrifuging the supernatant to obtain lentivirus;

2) placing the CHO cells on a 6-well plate and culturing the CHO cells overnight, diluting the lentivirus on the following day, infecting the CHO cells at a low MOI (multiplicity of infection) (MOI<1)(number of virus particles corresponding to each cell); sorting the cells with a flow cell sorter after 96 hrs from the infection, and inoculating the cells with the highest fluorescence intensity directly into a 96-well plate; observing the cells with a fluorescent microscope after the cells grow into monoclonal colonies one week later, selecting the brightest colony cells having a normal morphology and growth, and transferring the cells to a 24-well plate for expansion; transferring the cells to a 6-well plate when a confluence of nearly 90% is achieved, and finally transferring to a 10 cm culture dish; and freezing part of the cells and expanding the remaining cells;

3) searching out all gene integration sites of CHO cells in lentivirus with chromosome walking technology by using Lenti-X Integration Site Analysis Kit (Clontech: 631263).

Genomic DNA was digested overnight with three restriction enzymes: ADraI, SspI, and HpaI, by using several cell lines with the highest fluorescence intensity and normal cell morphology and growth rate as material. A reaction system of 100 μL was prepared with 2.5 Kg of genomic DNA and 80U of restriction enzyme, and was digested at 37° C. overnight (16-18 hours).

The digested product was purified and recovered with a DNA recovery kit. A ligation system for test was prepared with 4.8 μL of the digested genomic DNA, 1.9 μL of genome walker adaptor (25 μM) and 0.5 μL of T4 ligase, which is placed at 16° C. for ligation overnight. The ligation system was heated at 70° C. for 5 minutes to inactivate the ligase. 32 μL of TE buffer was added to each system to prepare corresponding library.

Two rounds of nested PCR were performed on the library to amplify the LTR region and adjacent genomic regions. Related steps for PCR reaction can be referred to the instructions of Lenti-X Integration Site Analysis Kit (Clontech: 631263) kit.

Finally, the PCR products were electrophoresed, and the main bands were cut and recovered for sequencing. After obtaining all the lentiviral integration information of each cell line, the relevant information of the CHO cell line with only a single copy of the lentivirus integration was select, and compared with the CHO-K1 genome information on BLAST to find out the integration site with high expression.

The present disclosure has the following advantages:

A site-specific integration method is used in the present application to integrate the target gene into a stable expression region at a specific site. The method can well address the problem of uncertain integration site caused by random integration, and effectively avoid repetitive screening for high-expressing monoclonal cells. Therefore, the method can effectively reduce development time of biopharmaceuticals to build stable expression cell lines, and thus reduce costs.

In the present disclosure, a protein gene is introduced at a fixed site of a CHO cell gene and stably expressed.

BRIEF DESCRIPTION OF THE DRAWINGS

The FIGURE shows a schematic diagram of the present disclosure.

DETAILED DESCRIPTION

The present disclosure is described in detail below with reference to the drawings and embodiments.

The FIGURE is a schematic diagram of a donor plasmid for integration to the site and a simulated schematic diagram of how to integrate to the site by homologous recombination. GOI as a target gene is integrated to a target site via two homologous recombination arms of 5'arm and 3' arm under a puromycin screening concentration of 4 μg/mL. In addition, the sequence upstream of 5'arm as a negative mark of screening can be used to remove monoclonal cells that are randomly integrated, such that recombinant CHO cells that are integrated at a specific site can be finally recovered.

Example 1

Selection of High Expression Site

Zsgreen1 gene was integrated at the base of No. 691045 in NW_006882077.1 gene of a cell. The obtained fluorescence cell was cultured for no less than 50 passages. The expression level was detected with a flow cytometry. The 50th generation of fluorescent cells still had a good green fluorescent protein expression level. The fluorescent signal was stably retained during the passage of the cells.

In addition, this fluorescent cell was also adapted to suspension, and the expression level of the fluorescent protein after adaption was detected again with a flow cytometry. The results show that among the recombinant CHO cells that are suspended over 50 passages, more than 95% maintains the expression level of the green fluorescent protein after suspension. It can be seen that the site is very stable and the fluorescent protein gene will not be lost due to passage of the cells.

Example 2

Selection of a Specific Target Sequence

According to proximity principle, the sequence of 5'CCAATGCTATTACCTTCTTCAGCATCTGTTCTT-GAAGACCTTCAGTCACTTTAGTTAA CTCTTC-CACTTTCGTTACTG-CAACTCTCA-GATCTAACTTGGCTTG 3', as shown in SEQ ID NO:7, was input into CRISRPRater System, and a target sequence with low off-target rate was predict and select. The parameter settings are as follows: 1) the maximum number of mismatched bases of the first 15 base pairs (bps) after NGG is 0; 2) the number of mismatched bases of all 21 bps after NGG is 2.

According to the above operation, the following sequence with a score of 0.87 is selected as the target sequence:

5'-GATCTAACTTGGCTTGCCTGAGG-3', as shown by SEQ ID NO:1; and according to the CRISPRater System, LOW efficacy (score<0.56); MEDIUM efficacy (0.56⇐score⇐0.74); and HIGH efficacy (score>0.74).

According to the CRISPRater System, all target sequences in the range of 690980-691090 near NW_006882077.1 have scores above 0.56, all of which are in the range of moderate or highly effective, and can be used as 5' GG3', as shown by SEQ ID NO:10 target sequence that can be identified by CRISPR/Cas9 technology.

Example 3 Selection of Promoters

The promoter of CMV (a strong promoter for expression in a mammalian cell derived from human cytomegalovirus) is replaced with various promoters including common promoters such as EF-1a (a strong promoter for expression in a mammalian cell derived from human elongation factor 1a), SV40 (a promoter for expression in a mammalian cell derived from simian vacuole virus 40), PGK1 (a promoter for expression in a mammalian cell derived from phosphoglycerate kinase gene), UBC (a promoter for expression in a mammalian cell derived from human ubiquitin C gene), human beta actin (a promoter for expression in a mammalian cell derived from β-actin gene), and CAG (a strong hybrid promoter for expression in a mammalian cell). It is determined by testing that the above promoters can regulate the downstream red fluorescence proteingene sequence and express the corresponding red fluorescence protein.

Example 4

The red fluorescence protein (DsRed, 26 KDa) is integrated at a specific site. For homologous recombination mediated by CRISPR/Cas9 later, sgRNA and donor plasmid were required to be constructed as follows.

1. First, the following sequence was synthesized for construction of SgRNA:

sgRNA-1fwd 5' TTTG-GATCTAACTTGGCTTGCCTGGT 3', as shown in SEQ ID NO:8; and sgRNA-1rev 5' TAAAACCAGGCAAGCCAAGTTA-GATC 3' as shown in SEQ ID NO:9.

1) The plasmid of PSK-u6-gRNA was digested with BBsI enzyme, and the resulted carriers were recovered;

2) synthetic fragments were annealed into double strands with sticky ends:

| sgRNA-1fwd (100 μM) | 4 μL |
| sgRNA-1rev (100 μM) | 4 μL |
| 10 × NEB buffer2 | 2 μL |
| H₂O | 10 μL |
| | 20 μL | by treated in a water bath at 95° C. for 5 min, and then naturally cooled to room temperature;

3) the fragments were joint and recombinant plasmids were constructed

| recycled linear carriers | 50 ng |
| annealed segments | 1 μL |
| 10 × T4 ligase buffer | 1 μL |
| T4 ligase | 1 μL |
| H₂O | |
| | to 10 μL ; |

4) joining at room temperature for more than 1 h, or at 4° C. overnight and conversion; and 5) cloning cells were selected and subjected to PCR identification, and the primer used for identification is M13—Synthetic primer R; those showing bands were identified as positive clones.

2. Construction of donor plasmid

The donor plasmid is described in the FIGURE in details: segments expect for GOI were synthesized; the sequence of 600 bps upstream and downstream of the target sequence is the sequence information of the left and right homology arms of the donor plasmid. The GOI is obtained by integrating HSA onto the donor plasmid with the existing C115 kit from Vazyme Biotech.

3. Cas9 (donated by Dr. Helene F Kildegaard from Technical University of Denmark), SgRNA and donor plasmid with a molar ratio of 1:1:1 were co-transfected into CHO cells cultured at 37° C. with 5% $CO_2$, and transfection reagent is Lipofectamine 3000 (Thermo Fisher Scientific). The method of transfection can be referred to instructions from the supplier. 4 μg/mL puromycin was then added into the resulted cells for screening for 10 days. MoFloXDP FACS machine (Beckman Coulter) was used to monoclonal cell sorting. Cells having red fluorescence but without green fluorescence are selected and inoculated into a 96-well plate.

4. After 2 weeks of growth, part of the cells was taken for identification with 5' junction PCR, 3'Junction PCR and out-out PCR, and keep positive cells.

Example 5

The glucagon-like peptide-1-human serum albumin fusion protein gene (NGGH, 75 KDa) was integrate at a specific site. In order to construct CRISPR/Cas9-mediated homologous recombination at a later stage, sgRNA and Donor Plasmid need to be constructed as below.

1. SgRNA was constructed as in example 4.

2. Construction of donor plasmid

The donor plasmid is described in the FIGURE in details: segments expect for GOI were synthesized; the sequence of 600 bps upstream and downstream of the target sequence is the sequence information of the left and right homology arms of the donor plasmid. The GOI is obtained by integrating HSA onto the donor plasmid with the existing C115 kit from Vazyme Biotech.

3. Cas9 (donated by Dr. Helene F Kildegaard from Technical University of Denmark), SgRNA and donor plasmid with a molar ratio of 1:1:1 were co-transfected into CHO cells cultured at 37° C. with 5% $CO_2$, and transfection reagent is Lipofectamine 3000 (Thermo Fisher Scientific). The method of transfection can be referred to instructions from the supplier. 4 μg/mL puromycin was then added into the resulted cells for screening for 10 days. MoFloXDP FACS machine (Beckman Coulter) was used to monoclonal cell sorting. Cells without any fluorescence are selected and inoculated into a 96-well plate.

4. After 2 weeks of growth, part of the cells was taken for identification with 5' junction PCR, 3'Junction PCR and out-out PCR, and keep positive cells.

Example 6

The antibody gene (Avastin, 160 KDa) was integrated at a specific site. In order to construct CRISPR/Cas9-mediated homologous recombination at a later stage, sgRNA and Donor Plasmid need to be constructed as below.
1. SgRNA was constructed as in example 4.
2. Construction of donor plasmid
The donor plasmid is described in the FIGURE in details: segments expect for GOI were synthesized; the sequence of 600 bps upstream and downstream of the target sequence is the sequence information of the left and right homology arms of the donor plasmid. The GOI is obtained by integrating Avastin onto the donor plasmid with the existing C115 kit from Vazyme Biotech.
3. Cas9 (donated by Dr. Helene F Kildegaard from Technical University of Denmark), SgRNA and donor plasmid with a molar ratio of 1:1:1 were co-transfected into CHO cells cultured at 37° C. with 5% $CO_2$, and transfection reagent is Lipofectamine 3000 (Thermo Fisher Scientific). The method of transfection can be referred to instructions from the supplier. 4 μg/mL puromycin was then added into the resulted cells for screening for 10 days. MoFloXDP FACS machine (Beckman Coulter) was used to monoclonal cell sorting. Cells without any fluorescence are selected and inoculated into a 96-well plate.
4. After 2 weeks of growth, part of the cells was taken for identification with 5' junction PCR, 3'Junction PCR and out-out PCR, and keep positive cells.

Example 7

The human serum albumin gene (HSA, 68 KDa) is integrated at a specific site. For homologous recombination mediated by CRISPR/Cas9 later, sgRNA and donor plasmid were required to be constructed as follows.
1. SgRNA was constructed as in example 4.
2. Construction of donor plasmid
The donor plasmid is described in the FIGURE in details: segments expect for GOI were synthesized; the sequence of 600 bps upstream and downstream of the target sequence is the sequence information of the left and right homology arms of the donor plasmid. The GOI is obtained by integrating Avastin onto the donor plasmid with the existing C115 kit from Vazyme Biotech.
3. Cas9 (donated by Dr. Helene F Kildegaard from Technical University of Denmark), SgRNA and donor plasmid with a molar ratio of 1:1:1 were co-transfected into CHO cells cultured at 37° C. with 5% $CO_2$, and transfection reagent is Lipofectamine 3000 (Thermo Fisher Scientific). The method of transfection can be referred to instructions from the supplier. 4 μg/mL puromycin was then added into the resulted cells for screening for 10 days. MoFloXDP FACS machine (Beckman Coulter) was used to monoclonal cell sorting. Cells without any fluorescence are selected and inoculated into a 96-well plate.
4. After 2 weeks of growth, part of the cells was taken for identification with 5' junction PCR, 3'Junction PCR and out-out PCR, and keep positive cells.

TESTING EXAMPLES

The four cell lines prepared in Examples 4-7 were tested by ELISA to observe whether the protein of interest was expressed and whether it was stable long-term expression.
Detection method: all four tests were performed by ELISA method. All selected positive cells were cultured in a 6-well plate and tested for long-term stably expressing the target protein with kits of Human Albumin ELISA Kit (RK00157) and Human IgG(Total) ELISA Kit(RK00393).
The cell line expression of the red fluorescence protein prepared in Example 4 was detected again with a flow cytometry, expression of red fluorescence was observed, and all the cells within 50 generations can stably express red fluorescent protein.
Detection method: cells at different passages were collected and detected directly with a flow cytometry, expression of red fluorescence was observed, and it was detected that more than 95% of the recombinant CHO cells at different passages expressed red fluorescence protein.
Good results were obtained for the above test in which the 5'-GATCTAACTTGGCTTGCCTGAGG-3', as shown by SEQ ID NO. 1, sequence is selected. Therefore, it shows that the target sequences in claims 5-9 can successfully construct a stable expression cell line by site-specific integration, and the protein of interest can be stably expressed for all cell lines.

SEQUENCE LISTING

The patent contains a lengthy sequence listing. A copy of the sequence listing is available in electronic form from the USPTO web site (https://seqdata.uspto.gov/?pageRequest=docDetail&DocID=US11732276B2). An electronic copy of the sequence listing will also be available from the USPTO upon request and payment of the fee set forth in 37 CFR 1.19(b)(3).

What is claimed is:
1. A method for stably expressing a protein at a predetermined site in a Chinese Hamster Ovary (CHO) cell genome, wherein the predetermined site in the CHO cell genome for stably expressing the protein is positioned at base of No. 691045 in a CHO cell gene comprising the nucleotide sequence of SEQ ID NO: 11; the method comprises:

identifying the sequence of SEQ ID NO: 10 in a base range of No. 690980-691090 in the CHO cell gene comprising the nucleotide sequence of SEQ ID NO: 11, around the predetermined site by CRISPR/Cas9 technology and position as a target sequence;

transforming the CHO cell with a recombinant donor carrier to obtain a recombine CHO cell;

culturing the recombinant CHO cell, and collecting a supernatant to detect the expression level of the protein, and adapting an adherent recombinant CHO cell to a suspension culture; and culturing the adapted recombinant CHO cell to express the protein.

2. The method according to claim 1, wherein the protein is one having a molecular weight of less than 160 KDa.

3. The method according to claim 1, wherein the protein is one selected from the group consisting of a polypeptide, a functional protein, an antibody, and a fusion protein.

4. The method according to claim 1, wherein the target sequence includes the bases positioned at No. 691068-691090 around the base of No. 691045 in the CHO cell gene comprising the nucleotide sequence of SEQ ID NO: 11, and the target sequence is the nucleotide sequence of SEQ ID NO: 1.

5. The method according to claim 1, wherein the target sequence is the nucleotide sequence of SEQ ID NO:2.

6. The method according to claim 1, wherein the target sequence is the nucleotide sequence of SEQ ID NO:3.

7. The method according to claim 1, wherein the target sequence is the nucleotide sequence of SEQ ID NO:4.

8. The method according to claim 1, wherein the target sequence is the nucleotide sequence of SEQ ID NO:5.

9. The method according to claim 1, wherein the target sequence is the nucleotide sequence of SEQ ID NO:6.

* * * * *